(12) United States Patent
Söring et al.

(10) Patent No.: US 7,608,054 B2
(45) Date of Patent: Oct. 27, 2009

(54) MEDICAL TREATMENT APPARATUS

(75) Inventors: Holger Söring, Quickborn (DE); Jörg Soring, Holm (DE)

(73) Assignee: Soering GmbH, Quickborn (DE)

( * ) Notice: Subject to any disclaimer, the term of this patent is extended or adjusted under 35 U.S.C. 154(b) by 918 days.

(21) Appl. No.: 10/624,581

(22) Filed: Jul. 22, 2003

(65) Prior Publication Data

US 2005/0020966 A1   Jan. 27, 2005

Related U.S. Application Data

(60) Provisional application No. 60/397,735, filed on Jul. 22, 2002.

(51) Int. Cl.
*A61B 17/20* (2006.01)
(52) U.S. Cl. .......................................................... 604/22
(58) Field of Classification Search .................. 604/27, 604/902, 35, 114, 28, 30, 107, 128, 127, 604/22; 606/6
See application file for complete search history.

(56) References Cited

U.S. PATENT DOCUMENTS

| | | | | |
|---|---|---|---|---|
| 3,805,787 A | * | 4/1974 | Banko | 604/22 |
| 4,804,364 A | * | 2/1989 | Dieras et al. | 604/22 |
| 4,982,730 A | | 1/1991 | Lewis, Jr. | |
| 5,984,889 A | * | 11/1999 | Christ et al. | 604/22 |
| 6,204,592 B1 | | 3/2001 | Hur | |
| 6,592,595 B1 | * | 7/2003 | Mallett et al. | 606/131 |

FOREIGN PATENT DOCUMENTS

| | | |
|---|---|---|
| DE | 4032471 | 4/1992 |
| DE | 3503098 | 3/1994 |
| DE | 3890213 | 8/1997 |

* cited by examiner

*Primary Examiner*—Nicholas D Lucchesi
*Assistant Examiner*—Christopher D Koharski
(74) *Attorney, Agent, or Firm*—Horst M. Kasper

(57) ABSTRACT

A medical treatment apparatus includes a hand piece (1) equipped with an ultrasound vibration generator and a sonotrode (3) attached to the hand piece (1). An adaptation sleeve (10) can be slid over the sonotrode (3) of the medical treatment apparatus. The adaptation sleeve (10) can be attached at the hand piece (1), wherein the adaptation sleeve (10) is equipped with a connector (12, 13) for receiving a suction hose (14). A separator (15) is furnished between a suction apparatus (A) and the suction hose (14).

23 Claims, 6 Drawing Sheets

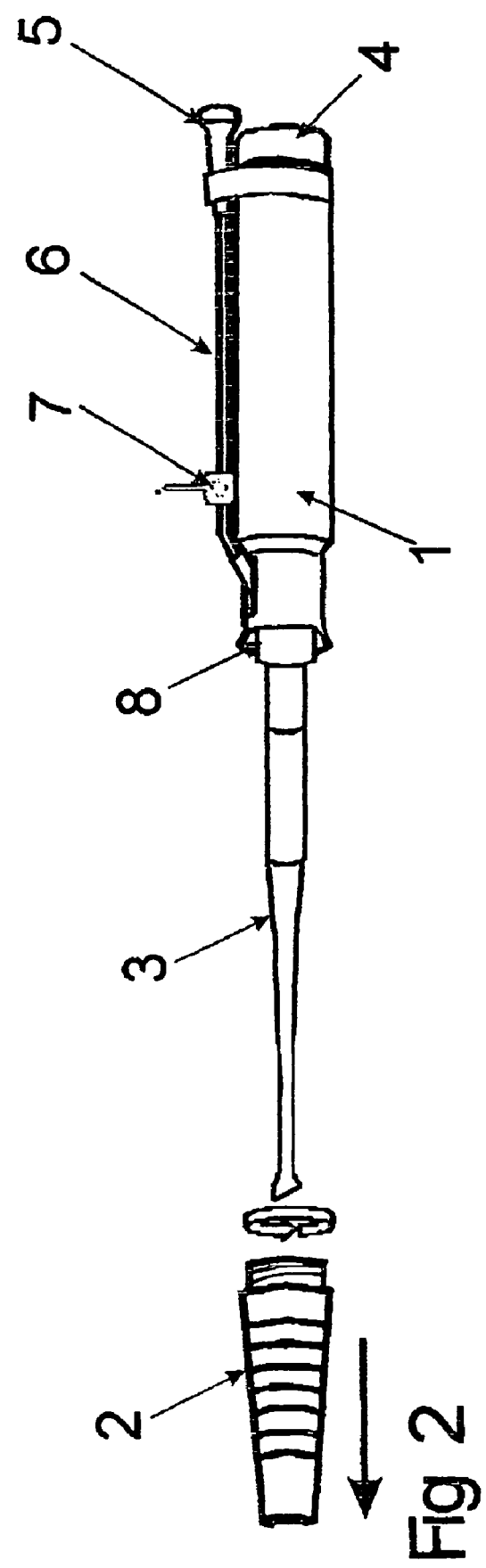

MEDICAL TREATMENT APPARATUS

CROSS REFERENCE TO RELATED APPLICATIONS

The present application includes the subject matter and claims the priority of provisional Patent Application Ser. No. 60/397,735 filed on Jul. 22, 2002 and entitled "Medical Treatment Apparatus".

FIELD OF THE APPLICATION

The invention relates generally to fume suction devices used in conjunction with sonotrodes.

Many apparatuses are employed which use the advantages of ultrasound technology, for example the piezoceramic principle or the magneto-strictive principle, in connection with the employment of such apparatus, for example for cutting and for treatment of wounds. Here preferably the piezoceramic principle is employed since this piezo ceramic principle generates much less heat as compared with the magnetostrictive principle.

DESCRIPTION OF RELATED ART

Bad smelling and damaging fume gases can be generated in connection with the use of such apparatus, which can interfere with the sight of the operator and can lead to an endangerment of the health by the release of damaging aerosols, toxic gases and human viruses.

Fume suction devices are installed in most operating theaters. The fume suction devices suck out the field of operation in the large area through a central ventilation device. Such fume sucking devices are not as useful today, so predominantly small apparatuses operated by an assistant are employed. Here a so-called suction funnel is held by hand in the neighborhood of the operating tool, such that vapors and fume gases generated during the thermal tissue coagulation and during electro-surgical cutting can be sucked off immediately at the field of generation. In addition the aerosols released during the bactericidal treatment of wounds are sucked off with the aid of such apparatus.

It is a disadvantage of this method that the sucking apparatus has to be held by an auxiliary person, wherein the auxiliary person then is not available for other activities.

SUMMARY OF INVENTION

It is an object of the invention to generate a medical treatment apparatus in particular for the treatment of wounds, which medical treatment apparatus does not exhibit the above described disadvantage, however can be employed with the same effectiveness.

This object is accomplished by sliding an adaptation sleeve over the sonotrode of the medical treatment apparatus and by attaching the adaptation sleeve at the hand piece, wherein the adaptation sleeve is furnished with a connector for receiving a suction hose.

The feed region of a sonotrode is covered with a sleeve screwed on the front region of the hand piece in a usual ultrasound apparatus, in particular for the bactericidal treatment or for the debridement of wounds. This sleeve can of course also be plugged or can be connected by way of a clamping cone or by a bayonet catch. After removal of the sleeve then the adapter part is set onto the hand piece and screwed on with a thread.

This adapter part is furnished with a receiver part for a suction hose, wherein the suction hose in turn is connected with a separating and depositing device. A further hose leads from this separating and depositing device to the suction device. The apparatus "Atmo-Safe™" produced and distributed by the company Atmos has proven to be a particular effectively working suction apparatus. The filter installed in this apparatus is tuned to such a fine degree that the smallest components up to the size of viruses can be filtered out.

BRIEF DESCRIPTION OF THE DRAWINGS

The treatment apparatus according to the present invention is now to be illustrated by way of an embodiment shown in the drawings.

DETAILED DESCRIPTION OF EMBODIMENTS OF THE INVENTION

Figure 1:
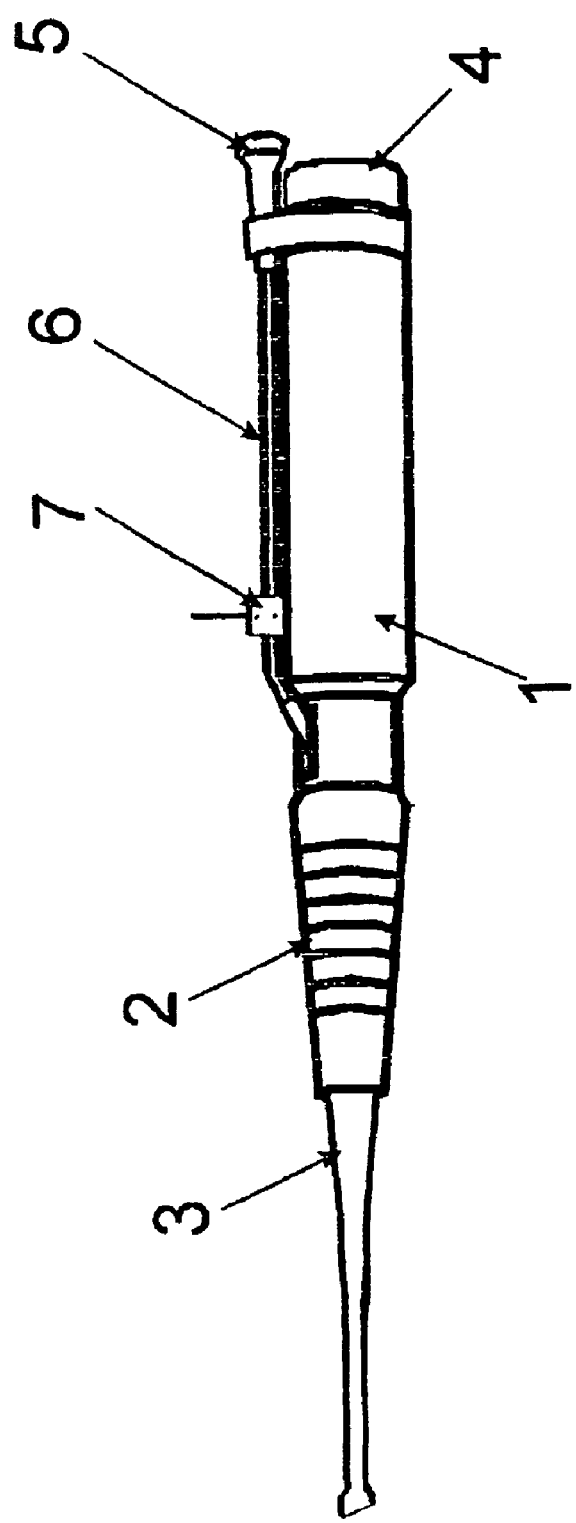
FIG. 1 a side elevation view of a hand piece with an inserted sonotrode.
Figure 2A:
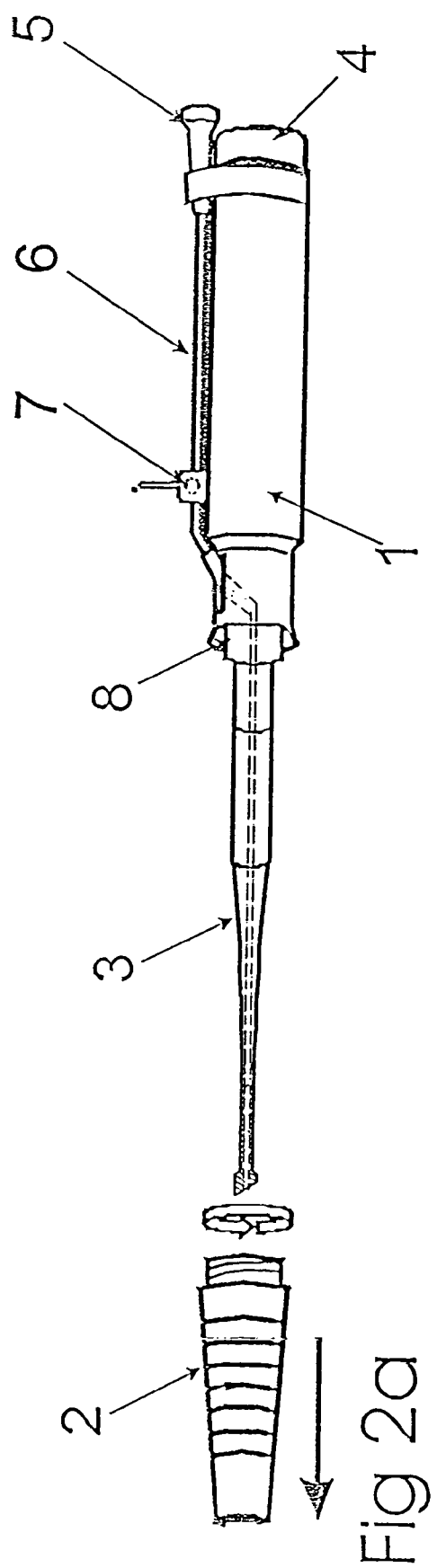
FIG. 2 the hand piece with a screwed off sleeve.
Figure 3:
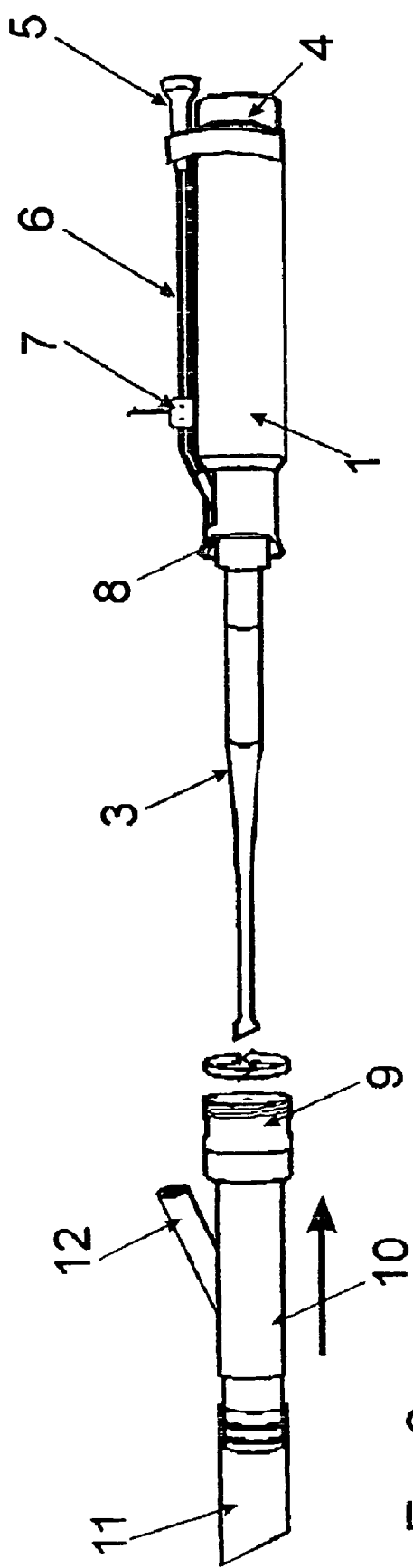
FIG. 3 a separate arrangement of hand piece and adaptation part.
Figure 4:
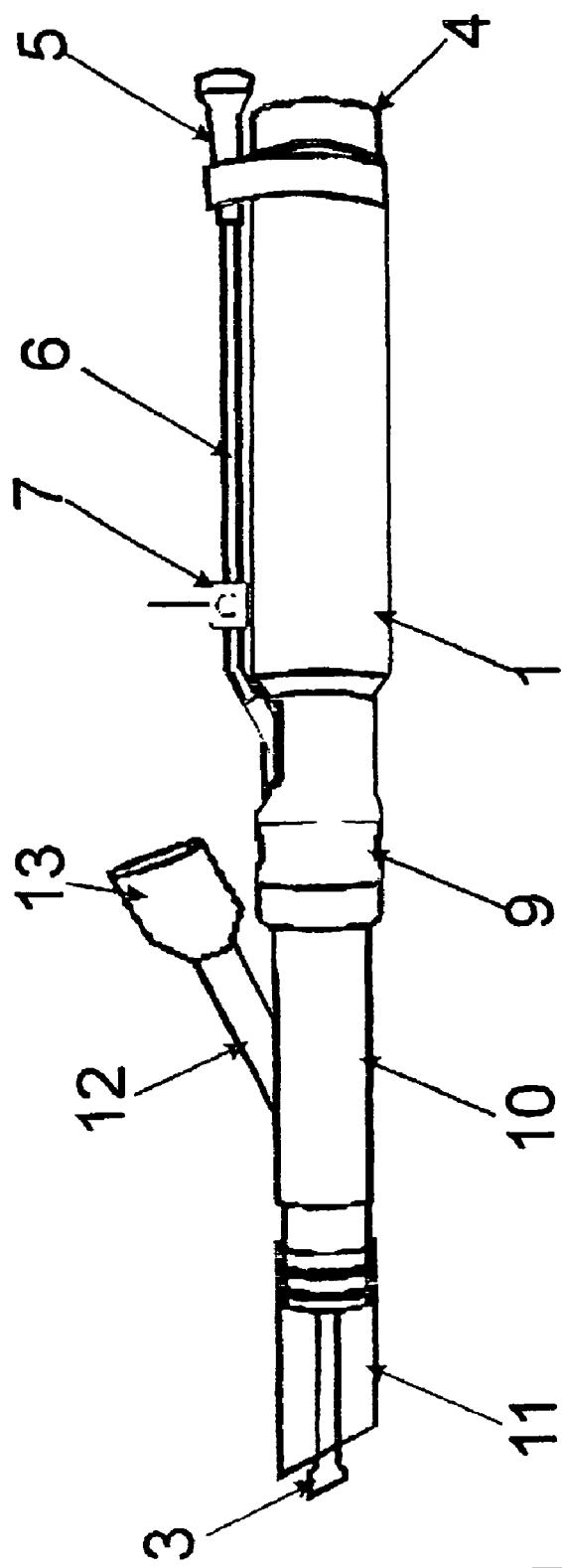
FIG. 4 a side elevation view of a hand piece with a screwed on adaptation device.
Figure 5:
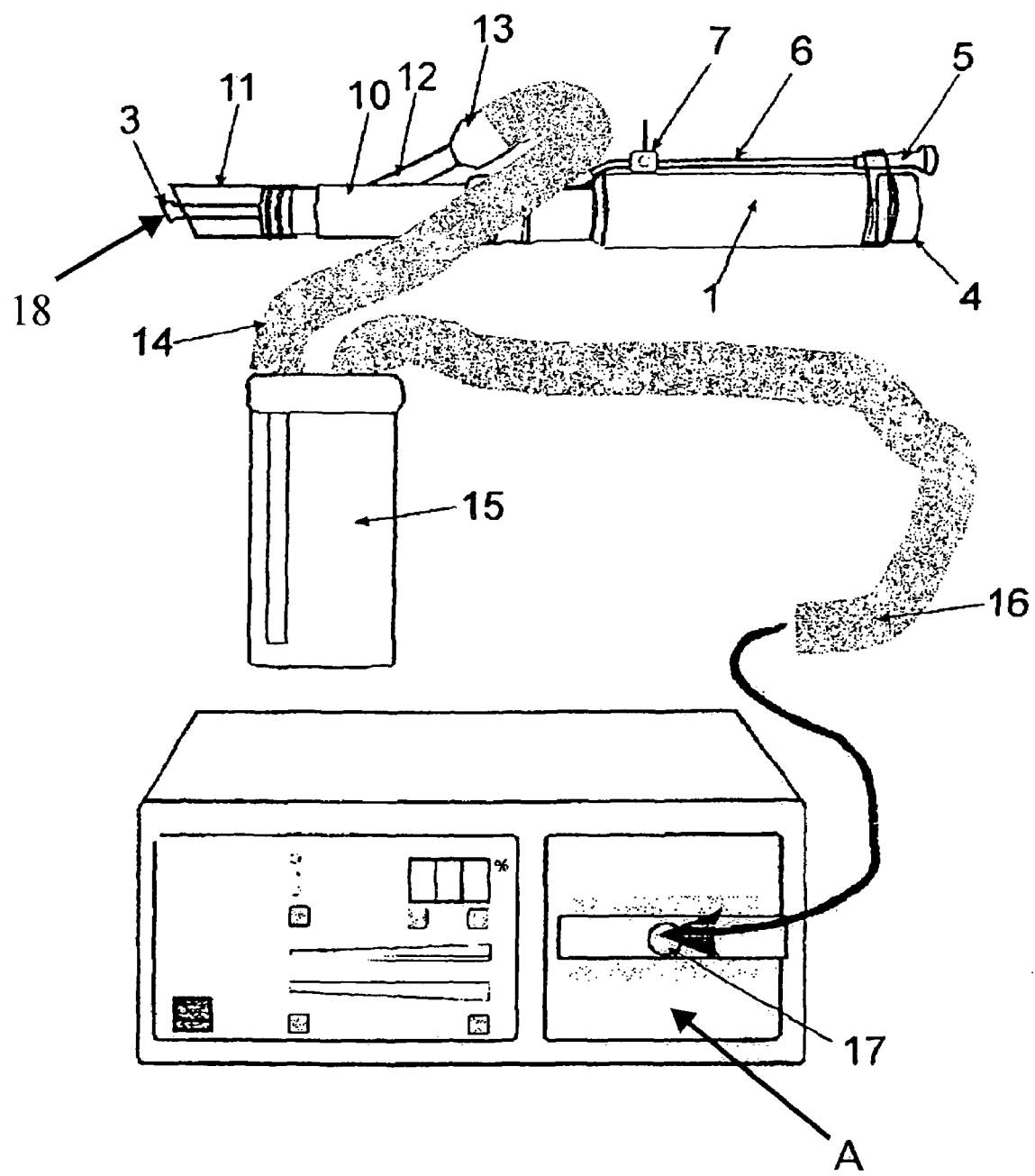
FIG. 5 a complete set up of a suctioning device.

The medical treatment apparatus as illustrated in FIG. 1 comprises a hand piece (1) with a connector (5) for the connection line to the storage container for flushing liquid such as rock salt solution and others and also medical healing agents such as heparin, antibiotics and the like, wherein the flushing liquid and the medical healing agents are then fed to the tip of the sonotrode through the flushing line (6) and the valve (7) and through a channel within the sonotrode (3) equipped with an ultrasound vibration generator operating from a frequency region of from 5 kHz to 60 kHz and preferably from 15 kHz to 30 kHz. The ultrasound energy is fed to the hand piece through the electro-connection (4) in a conventional way.

The hand piece is further equipped with a sonotrode receiver, wherein a sonotrode (3) is exchangeably screwed into the sonotrode receiver. The attachment region of the sonotrode is covered with a sleeve (2), wherein the sleeve can be removed with an attachment thread. Preferably, the sleeve (2) with its attachment thread is screwed into the inner cylindrical thread (8) of the hand piece (1). The adapter part can be attached to the hand piece (1) by way of the attachment thread (9) after the screwing off and the removal of the sleeve (2).

This adapter part comprises a connection bush (9), with the connection bush (9) transitioning into the adaptation sleeve (10). The receiver part (12) with the hose connection (13) is disposed at this adaptation sleeve (10) and the suction tube (11) is attached at the oppositely disposed end.

The suction hose (14) is inserted into the hose connection (13), with the hose (14) ending in the separator (15). This separator (15) filters the large aerosol components out in a first step. This can be liquids or also solid components. Such separator (15) is primarily employed to care for the main filter disposed in the suction apparatus (A). The separator (15) can here be a conventional water trap or a HEPA-filter. Such a suction apparatus (A) is for example offered and distributed by the company Atmos under the Trademark AtmoSafe™.

The suction tube (11) attached at the adaptation sleeve (10) can be produced out of a transparent plastic in order to improve the view ability for the medical doctor onto the treatment field. The separator (15) is connected to the suction apparatus (A) through the connection tube (16) and through the connector (17).

APPENDIX

List of References Numerals

A suction apparatus:
1 hand piece
2 sleeve
3 sonotrode
4 electro-connection
5 connection for flushing liquid
6 flushing line
7 valve
8 thread
9 connection bush
10 adaptation sleeve
11 suction tube
12 receiver part
13 hose connection
14 hose
15 separator
16 connection hose

The invention claimed is:

1. A medical treatment apparatus comprising
a hand piece (1);
an ultrasound generator,
electrical connection means (4) attached to a rear end of the hand piece (1) and connected to the ultrasound generator and for feeding electrical energy to the ultrasound generator;
a connector (5) disposed near the rear end of the hand piece (1) for connecting a line to a storage container for a medical flushing liquid;
a sonotrode (3) having a tip and having a rear end attached to the front end of the hand piece (1), and wherein the ultrasound generator is connected to and drives the sonotrode (3) with ultrasound;
a flushing line (6) having a rear end connected to the connector for medical flushing liquid to the tip of the sonotrode, wherein the flushing line is aligned relative to an axis of symmetry of the hand piece;
a valve (7) disposed in the flushing line (6);
a channel disposed within the sonotrode (3) for feeding a medical flushing liquid to a front tip of the sonotrode (3) and wherein the channel is connected to a front end of the flushing line (6);
an inner cylindrical thread (8) disposed at a front end of the hand piece (1);
an adaptation sleeve (10) supporting an outer attachment thread on a rear end for attachment to the inner cylindrical thread (8) of the front side of the hand piece (1), wherein the adaptation sleeve (10) is slid over the sonotrode (3) and attached to the hand piece (1);
a suction tube (11) slid over the sonotrode (3), surrounding a front end of the sonotrode (3) and attached to a front end of the adaptation sleeve (10) for suctioning waste medical flushing liquid;
a receiver part (12) disposed with a first end at and branching sideways from the adaptation sleeve (10) for feeding the waste medical flushing liquid;
a hose connection (13) disposed with a first end at a second end of the receiver part (12);
a suction hose (14), wherein a first end of the suction hose (14) is inserted into the hose connection (13);

a separator (15), wherein a second end of the suction hose (14) is inserted into the separator;
a suction apparatus (A);
a connector (17) disposed at the suction apparatus (A);
a connection tube (16), wherein the connection tube connects the separator (15) and the connector (17) of the suction apparatus (A).

2. The medical treatment apparatus according to claim 1 wherein a treatment face (18) of the sonotrode (3) is disposed clearly outside of the front edge of the suction tube (11).

3. The medical treatment apparatus according to claim 1 wherein the flushing line (6) serves for flushing healing agents to the tip of the sonotrode, wherein the flushing line is aligned relative to an axis of symmetry of the hand piece; and the valve (7) disposed in the flushing line (6) near a front end of the flushing line (6).

4. The medical treatment apparatus according to claim 1 wherein the apparatus is set for frequency region from 5 kHz to 60 kHz and preferably from 15 kHz to 30 kHz.

5. The medical treatment apparatus according to claim 1 for the treatment of septic wounds and/or debridement comprising the ultrasound generator, the hand piece and the sonotrode attached to the hand piece wherein the ultrasound generator operates according to the magneto strictive principle.

6. The medical treatment apparatus according to claim 1, wherein a suction tube out of opaque or transparent material is plugged onto the front end of the adaptation sleeve (10).

7. The medical treatment apparatus according to claim 1, further
comprising a main filter disposed in the suction apparatus (A).

8. The medical treatment apparatus according to claim 1, wherein
the separator (15) is a conventional water trap or a HEPA-filter.

9. The medical treatment apparatus according to claim 1, wherein
the ultrasound generator operates according to the piezo ceramic principle and is set for frequency region of from 5 kHz to 60 kHz.

10. The medical treatment apparatus according to claim 1, wherein
the ultrasound generator operates according to the magneto-strictive principle is set for frequency region of from 5 kHz to 60 kHz.

11. A medical treatment apparatus comprising a hand piece (1);
an ultrasound generator disposed in the hand piece (1),
electrical connection means (4) attached to a rear end of the hand piece (1) and connected to the ultrasound generator and for feeding electrical energy to the ultrasound generator;
a connector (5) disposed near the rear end of the hand piece (1) for connecting a line to a storage container for a flushing healing agent;
a sonotrode (3) having a tip and having a rear end attached to the front end of the hand piece (1), and wherein the ultrasound generator is connected to and drives the sonotrode (3) with ultrasound;
a flushing line (6) having a rear end connected to the connector for flushing healing agent to the tip of the sonotrode, wherein the flushing line is aligned relative to an axis of symmetry of the hand piece;

a valve (7) disposed in the flushing line (6),
a channel disposed within the sonotrode (3) for feeding a flushing healing agent to a front tip of the sonotrode (3) and wherein a rear end of the channel is connected to a front end of the flushing line (6);
an inner cylindrical thread (8) disposed at a front end of the hand piece (1);
a connection bush (9) having an outer attachment thread on a rear end for attachment to the inner cylindrical thread (8) of the front side of the hand piece (1);
an adaptation sleeve (10), wherein a front end of the connection bush (9) transitions into a rear end of the adaptation sleeve (10); wherein the connection bush (9) and the adaptation sleeve (10) are slid over the sonotrode (3) and attached to the hand piece (1);
a suction tube (11) slid over the sonotrode (3), surrounding a front end of the sonotrode (3) and attached to a front end of the adaptation sleeve (10) for suctioning discharge flushing healing agent;
a receiver part (12) disposed with a first end at and branching sideways from the adaptation sleeve (10) for discharging the discharge flushing healing agent;
a hose connection (13) disposed with a first end at a second end of the receiver part (12);
a suction hose (14) attached with a first end to a second end of the hose connection (13) of the adaptation sleeve (10).

12. The medical treatment apparatus according to claim 11 for the treatment of septic wounds and/or debridement comprising the ultrasound generator, the hand piece and the sonotrode attached at the hand piece, wherein the ultrasound generator operates according to the piezo ceramic principle.

13. The medical treatment apparatus according to claim 11 wherein a separator (15) is furnished between a suction apparatus (A) and the suction hose (14).

14. The medical treatment apparatus according to claim 11 wherein the suction tube (11) out of an opaque or a transparent material is plugged onto the front end of the adaptation sleeve (10).

15. The medical treatment apparatus according to claim 11, wherein the flushing line (6) runs along an outside of the handle (1) and changes over to an axial position relative to the handle (1) at the front end of the handle (1) toward the sonotrode (3) and wherein an end of the flushing line (6) toward the sonotrode connects to the channel.

16. The medical treatment apparatus according to claim 11 wherein a separator (15) is furnished between a suction apparatus (A) and the suction hose (14) and wherein the waste medical flushing liquid is guided outside of and separate from the hand piece (1).

17. The medical treatment apparatus according to claim 11, wherein a treatment surface (18) of the sonotrode (3) is disposed clearly outside of the front edge of the suction tube (11).

18. The medical treatment apparatus according to claim 11, wherein the apparatus is set for frequency region of from 5 kHz to 60 kHz and preferably from 15 kHz to 30 kHz.

19. A medical treatment apparatus kit comprising
a hand piece (1);
an ultrasound generator disposed in the hand piece (1),
electrical connection means (4) attached to a rear end of the hand piece (1) and connected to the ultrasound generator and for feeding electrical energy to the ultrasound generator;
a connector (5) disposed near the rear end of the hand piece (1) for connecting a line to a storage container for a medical flushing liquid;
a sonotrode (3) having a tip and having a rear end attached to the front end of the hand piece (1), and wherein the ultrasound generator is connected to and drives the sonotrode (3) with ultrasound;
a flushing line (6) having a rear end connected to the connector for flushing healing agents to the tip of the sonotrode, wherein the flushing line is aligned relative to an axis of symmetry of the hand piece;
a valve (7) disposed in the flushing line (6),
a channel disposed within the sonotrode (3) for feeding a medical flushing liquid to a front tip of the sonotrode (3) and wherein the channel is connected to a front end of the flushing line (6);
an inner cylindrical thread (8) disposed at a front end of the hand piece (1);
wherein the hand piece (1), the ultrasound generator, the electrical connection means (4), the connector (5), the flushing line (6), the valve (7), the inner cylindrical thread (8), the sonotrode (3), and the channel form a base part of a kit;
a connection bush (9) having an outer attachment thread on a rear end for attachment to the inner cylindrical thread (8) of the front side of the hand piece (1);
an adaptation sleeve (10), wherein a front end of the connection bush (9) transitions into a rear end of the adaptation sleeve (10); wherein the connection bush (9) and the adaptation sleeve (10) are slid over the sonotrode (3) and attached to the hand piece (1);
a suction tube (11) slid over the sonotrode (3), surrounding a front end of the sonotrode (3) and attached to a front end of the adaptation sleeve (10) for suctioning waste medical flushing liquid;
a receiver part (12) disposed with a first end at and branching sideways from the adaptation sleeve (10) for feeding the waste medical flushing liquid;
a hose connection (13) disposed with a first end at a second end of the receiver part (12);
a suction hose (14) attached with a first end to a second end of the hose connection (13) of the adaptation sleeve (10);
wherein the connection bush (9), the adaptation sleeve (10), the suction tube (11), the receiver part (12), the hose connection (13), and the suction hose (14) form a first attachment of the kit;
a sleeve (2) having an outer attachment thread on a rear end for attachment to the inner cylindrical thread (8) at the front side of the hand piece (1), wherein the sleeve (2) is slid over the sonotrode (3) and attached to the hand piece (1);
wherein the sleeve (2) forms a second attachment of the kit.

20. The medical treatment apparatus kit according to claim 19 wherein a separator (15) is furnished between a suction apparatus (A) and the suction hose (14).

21. The medical treatment apparatus kit according to claim 19 wherein the suction tube (11) made out of an opaque or transparent material is plugged onto the front end of the adaptation sleeve (10).

22. The medical treatment apparatus kit according to claim 19 wherein the apparatus is set for frequency region of from 5 kHz to 60 kHz and preferably from 15 kHz to 30 kHz.

23. The medical treatment apparatus kit according to claim 19 wherein a treatment surface (18) of the sonotrode (3) is disposed clearly outside the front edge of the suction tube (11), wherein the receiver part (12), the hose connection (13), and the suction hose (14) are generally disposed at a distance from the hand piece (1).

* * * * *